United States Patent
Basiony

(10) Patent No.: US 10,709,868 B2
(45) Date of Patent: Jul. 14, 2020

(54) CURVED SPLIT-TIP CATHETER

(71) Applicant: Mohamed A Basiony, Kenmore, WA (US)

(72) Inventor: Mohamed A Basiony, Kenmore, WA (US)

(*) Notice: Subject to any disclaimer, the term of this patent is extended or adjusted under 35 U.S.C. 154(b) by 179 days.

(21) Appl. No.: 16/017,505

(22) Filed: Jun. 25, 2018

(65) Prior Publication Data

US 2019/0388648 A1 Dec. 26, 2019

(51) Int. Cl.
*A61M 25/00* (2006.01)
*A61M 1/36* (2006.01)

(52) U.S. Cl.
CPC ...... *A61M 25/007* (2013.01); *A61M 25/0026* (2013.01); *A61M 25/0071* (2013.01); *A61M 1/3661* (2014.02); *A61M 25/001* (2013.01); *A61M 2025/0034* (2013.01); *A61M 2210/12* (2013.01)

(58) Field of Classification Search
CPC ............ A61M 25/007; A61M 25/0026; A61M 25/003; A61M 2025/034; A61M 25/0067; A61M 25/0071; A61M 25/0032; A61M 2025/0031
See application file for complete search history.

(56) References Cited

U.S. PATENT DOCUMENTS

| 4,626,240 A | * | 12/1986 | Edelman | A61M 5/1582 604/43 |
| 2007/0225661 A1 | * | 9/2007 | Ash | A61M 25/0021 604/284 |
| 2015/0306302 A1 | * | 10/2015 | Marsden | A61M 1/3661 604/95.04 |

* cited by examiner

*Primary Examiner* — Matthew F Desanto

(57) ABSTRACT

A hemodialysis curved split-tip catheter comprises an elongated portion, a proximal end and a distal end defining a longitudinal axis. The proximal end attaches to a hub with suture wings assembly, which in turn connected to extension tubings. The distal end has two distal tip segments splitted from each other. The distal tip segments bend longitudinally inward toward a centerline of a blood vessel. First distal tip segment has a smaller angle, with respect to the axis extended from the dividing point longitudinally parallel to a centerline axis of a blood vessel, compare to second distal tip segment. This configuration to make the distal end of the catheter to be located not at the centerline axis of a blood vessel.

6 Claims, 5 Drawing Sheets

CURVED SPLIT-TIP CATHETER

BACKGROUND

Curved split-tip catheters were designed to utilize independent "free floating" distal tip segments that were separated at a distal tip of the catheters to may reduce the likelihood of potential occlusion and sucking during dialysis treatment.

In a reverse blood lines configuration, these catheters may have more than 20% of a blood recirculation.

Therefore, it would be desirable to design a curved split-tip catheter that may minimize a blood recirculation during dialysis in forward and reverse blood lines configurations.

SUMMARY

Accordingly, a hemodialysis curved split-tip catheter is described to may address recirculation issues.

The catheter may comprise an elongated portion, a proximal end and a distal end defining a longitudinal axis. Distal end may have two distal tip segments that may split (separated) from each other with respect to a longitudinal axis. A proximal end of said two distal tip segments may be coupled with a distal end of elongated portion.

First distal tip segment and second distal tip segment bend longitudinally inward toward the centerline of a blood vessel. Each bend (curvature) may have a different angle with respect to the axis that may extend from a dividing point longitudinally parallel to a blood vessel centerline axis. First distal tip segment may have a longer length and a smaller angle with respect to second distal tip segment.

First distal tip segment may have a first distal tip opening with a straight tip, while second distal tip segment may have a side opening and a sealed portion. Sealed portion may start from a side hole till a tip of second distal tip segment. Also, sealed portion may be completely sealed with respect to a blood flow.

Elongated portion may have an exterior with generally round, oval or any other shapes in cross section. Also, elongated portion may have an internal longitudinally extending lumen of D-shape, or circular, or any other shapes. Each distal tip segment may have a D-shape or circular, or any other shapes in cross section.

Proximal end of the catheter may attach to a hub with suture wings assembly, which in turn may be connected to extension tubings. Extension tubings may fluidly connect catheter lumens to a blood treatment unit or a dialysis machine.

BRIEF DESCRIPTION OF THE DRAWINGS

The accompanying drawings, which are incorporated in, and constitute a part of the specification, illustrate or exemplify embodiment of the present disclosure and, together with the description, generally explain the principles and features of the present disclosure. The reader should understand that no limitation to the precise arrangement and instrumentalities shown. Modifications, alternation and further application of the principles of the disclosure are also included in the scope of this disclosure. The drawings are briefly described as follows.

DETAILED DESCRIPTION

The following detailed description illustrates the principal of the disclosure by way of example not by way of limitation. While a reference use of the present disclosure describes a curved split-tip catheter to be used in hemodialysis, additional non-limiting usage would also include hemofiltration, hemodifiltration, blood adsorption, apheresis, as those of ordinary skill in the art will readily understand.

The hemodialysis curved split-tip catheter of present disclosure can be utilized as a short term or long term vascular access for the above treatments and may be made by a biocompatible material like; polyethene, Silicon or any other suitable material. The catheter may also include an anti-microbial coating such as silver, methylene blue and the like. The catheter may be of any suitable size between 6 to 16 French circumferences, or any other suitable size.

The configuration of the catheter may be manipulated to facilitate placement of the catheter into a blood vessel. In one implementation, the catheter may be compressed into a substantially liner profile using a sheath. In an alternative implementation, the catheter may be placed over a guidewire (sheathless technique) with or without stylet to facilitate placement of the catheter into a blood vessel. In this implementation, first distal tip segment may have a self-sealed side hole and a sealed portion of a second distal tip segment may have also a self-sealed hole.

Figure 1:
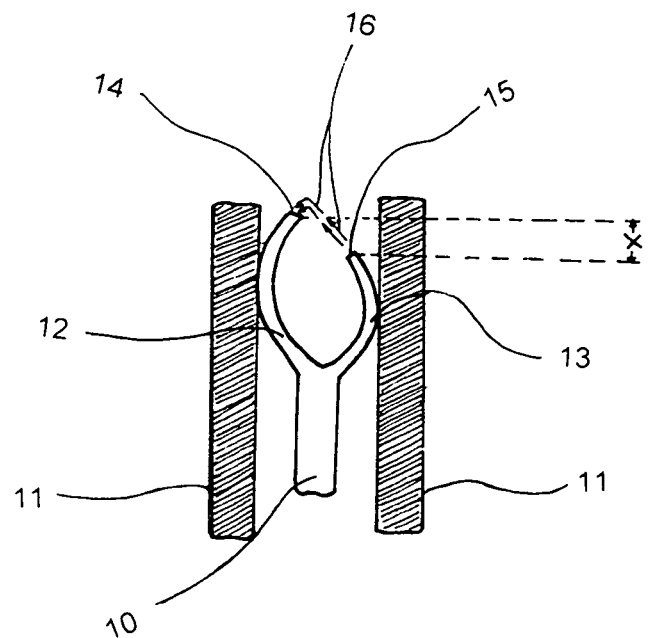
FIG. 1 illustrates a prior art curved split-tip catheter with a blood recirculation in a reverse blood lines configuration according to the present disclosure.

Now referring to FIG. 1, it illustrates a prior art curved split-tip catheter 10, a first distal tip segment 12, a second distal tip segment 13 and a blood vessel wall 11. First distal tip segment 12 may have a distal tip opening 14 and a second distal tip segment 13 may a distal tip opening 15. Arrows 16 represent a blood recirculation from a second distal tip opening 15 of a second distal tip segment 13 to a first distal tip opening 14 of a first distal tip segments 12 in a reverse blood lines configuration. This re-circulation may be more than 20%. "X" represents a distance between a first distal tip opening 14 of a first distal tip segment 12 and a second distal tip opening 15 of a second distal tip segment 13. In the prior art this distance may be about 10 mm to about 25 mm.

Figure 2:
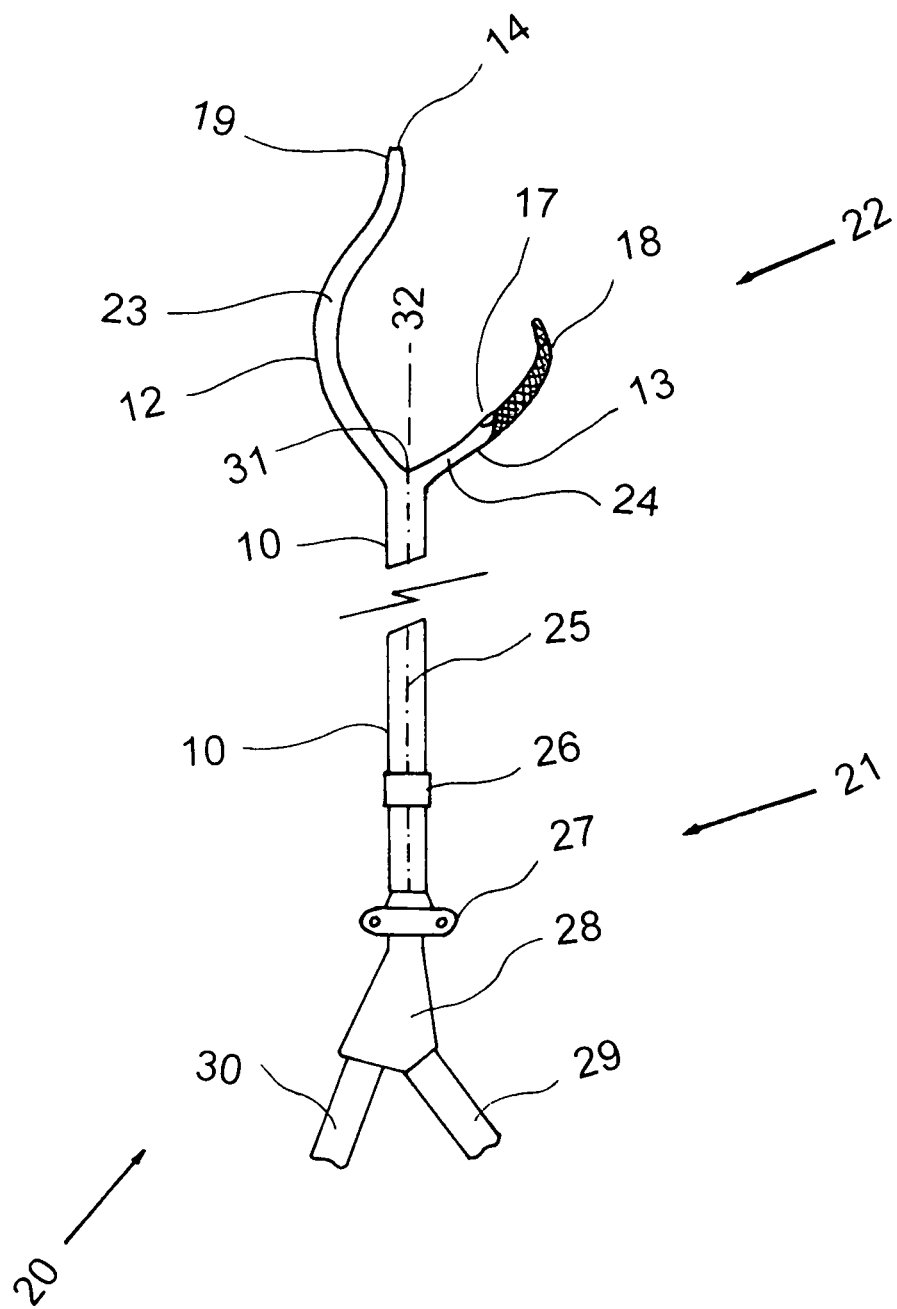
FIG. 2 is a perspective view of a hemodialysis curved split-tip catheter according to the present disclosure.

FIG. 2 illustrates a catheter 20 that may comprise an elongated portion (catheter body) 10, a proximal end 21 and a distal end 22, extended longitudinally to form a longitudinal axis 32. Elongated portion (catheter body) 10 can be straight or have a pre-curved configuration.

Proximal end 21 of a catheter 20 may have a cuff 26 (that may be polyester felt or any other material) and a hub 28 with suture wings 27, which in turn may be connected to extensions tubings 29 and 30 as is standard in dialysis catheters. The extension tubes 29 and 30 fluidly connect catheter lumens 23 and 24 to a blood treatment unit or a dialysis machine (not shown for simplicity).

Distal end 22 of a catheter 20 may be splitted (separated) with respect to a longitudinal axis 32 into a first distal tip segment 12 and a second distal tip segment 13 at a dividing point 31. First distal tip segment 12 and second distal tip segment 13 bend longitudinally inward toward a longitudinal axis 32. First distal tip segment 12 may have a lumen 23, a straight tip 19 and a first distal tip opening 14.

A second distal tip segment 13 may have a side opening 17, a sealed portion 18 and a lumen 24. The sealed portion may start from a side opening 17 to a tip of second distal tip segment 13. It may be completely sealed with respect to a blood flow and it may be created to may allow a smooth blood flow through a side opening 17 of a second distal tip segment 13 without any blood accumulation near to a side opening 17.

Figure 3:
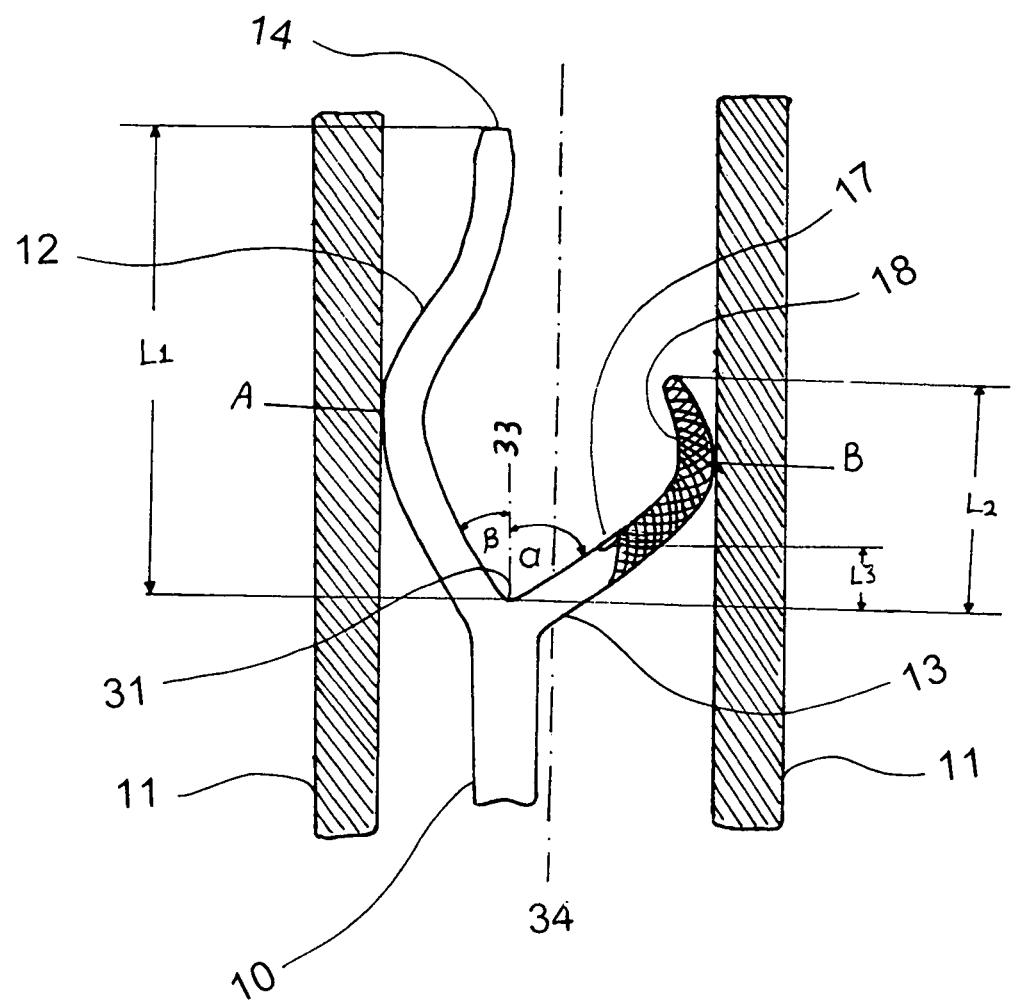
FIG. 3 is an enlarged plan view of a distal portion of the catheter of FIG. 2 within a blood vessel according to the present disclosure.

FIG. 3 illustrates a non-centric configuration of a distal end 22 of a catheter 20 with respect to a blood vessel centerline axis 34, wherein an elongated portion (catheter body) 10, a blood vessel wall 11, a first distal tip segment 12 with a first distal tip opening 14 and a second distal tip segment 13 with a side opening 17 and a sealed portion 18.

"α" represents an angle of a second distal tip segment 13 with respect to axis 33 that may extend from a dividing point 31 longitudinally parallel to a blood vessel centerline axis 34 and "β" may be an angle of a first distal tip segment 12 with respect to axis 33 that may extend from a dividing point 31 longitudinally parallel to a blood vessel centerline axis 34. These angles to may place a distal end 22 of a catheter 20 not at a blood vessel centerline axis 34 (non-centric). Angle "α" may be about 40 degrees to about 80 degrees while "β" may be about 10 degrees to about 30 degrees or any other suitable degrees.

FIG. 3 also illustrates points "A" & "B" that may be contact points with a blood vessel wall 11. This configuration to may make a first distal tip opening 14 of a first distal tip segment 12 and a side opening 17 of a second distal tip segment 13 away from a blood vessel wall 11 to may minimize fibrin sheath formation or thrombus around first distal tip opening 14 and a side opening 17. Lateral distance between such two points may be about 5 mm to about 20 mm, or any other suitable distance.

Also, in FIG. 3, a first distal tip segment 12 may be extended longitudinally from a dividing point 31 to a first distal tip opening 14 with a length of "L1" while a second distal tip segment 13 may be extended longitudinally from a dividing point 31 to a tip of a sealed portion 18 with a length of "L2". "L1" may be about 30 mm to about 60 mm, or any other suitable length, while "L2" may be about 5 mm to about 20 mm or any other suitable length. Length "L3" is a lateral length from a dividing point 31 to a side hole 17 of a second distal tip segment 13. "L3" may be about 30% to about 50% of "L2" or any other suitable percentage.

Figure 4:
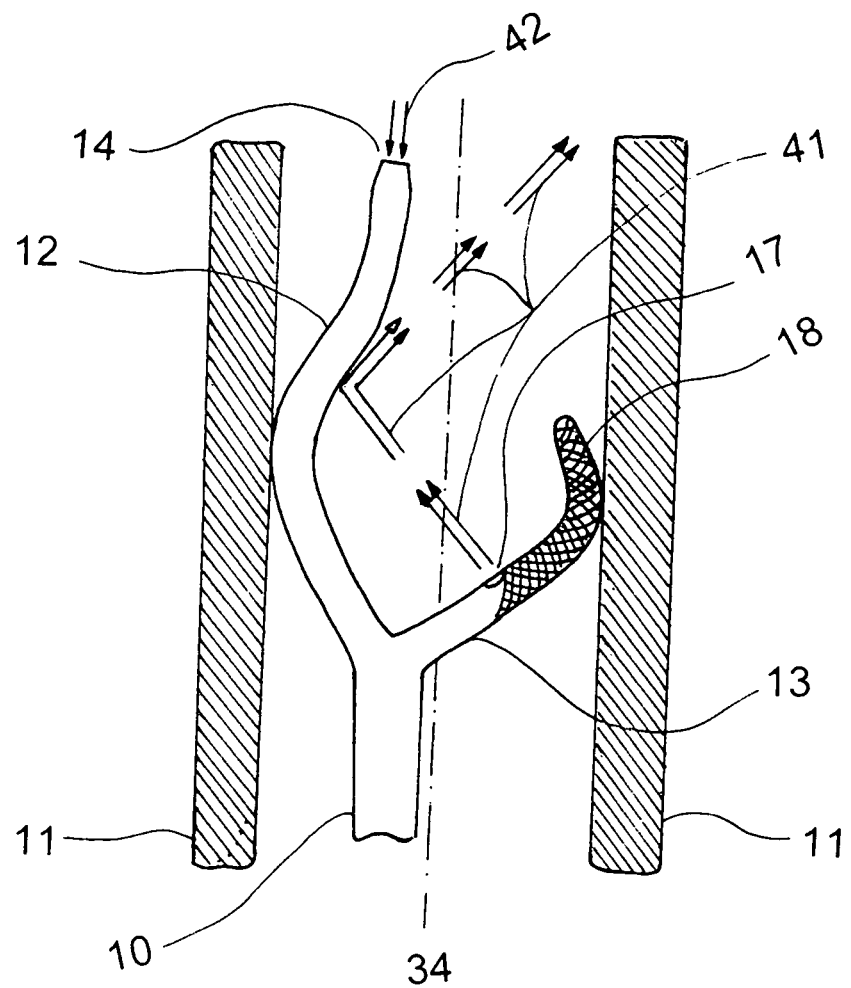
FIG. 4 is an enlarged plan view of a distal portion of the catheter of FIG. 2 within a blood vessel in a reverse blood lines configuration according to the present disclosure.

FIG. 4 illustrates a distal end 22 of a catheter 20 in a reverse blood lines configuration, wherein an elongated portion (catheter body) 10, a first distal tip segment 12 with a first distal tip opening 14, a second distal tip segment 13 with a side opening 17 and a sealed portion 18, a blood vessel wall 11 and a blood vessel centerline axis 34.

Also, in FIG. 4, arrows 41 represents a blood outlet from a side opening 17 of a second distal tip segment 13 while arrows 42 represents a blood inlet to a first distal tip opening 14 of a first distal tip segment 12 in a reverse blood lines configuration. As it is being understood, the kinetic energy of a blood flowing out from a side opening 17 may deliver it away from a blood inflow to a first distal tip opening 14 after it may have been reflected by a blood vessel wall 11.

Figure 5:
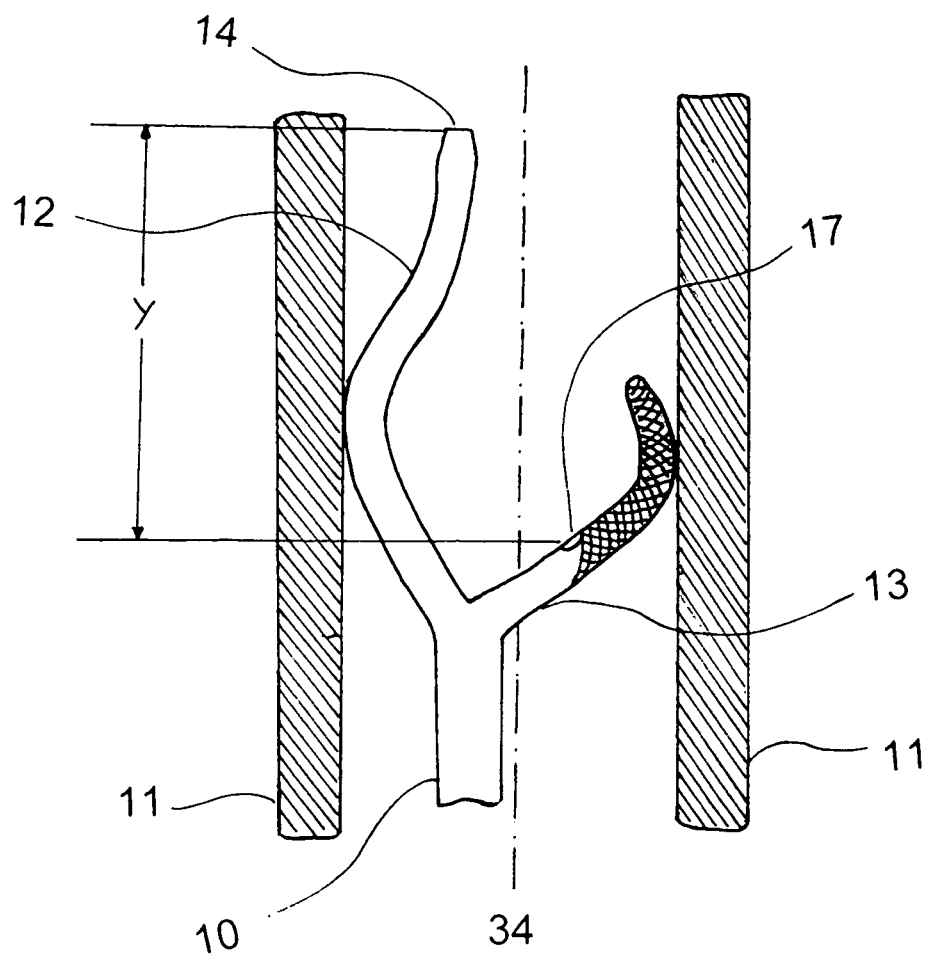
FIG. 5 is an enlarged plan view of a distal portion of the catheter of FIG. 2 within a blood vessel to illustrate a lateral distance between the two distal tip openings according to the present disclosure

FIG. 5 illustrates a distal end 22 of a catheter 20 wherein an elongated portion (catheter body) 10, a blood vessel wall 11 and a blood vessel centerline axis 34. FIG. 5, also illustrates a distance "Y" between a first distal tip opening 14 of a first distal tip segment 12 and a side opening 17 of a second distal tip segment 13 of a catheter 20. Distance "Y" may be about 30 mm to about 45 mm or any other suitable distance.

Comparing FIG. 1 and FIG. 4 in a reverse blood lines configuration, those skilled in the art will recognize that kinetic energy of a blood flowing out from a side opening 17 may deliver it away from a blood inflow to a first distal tip opening 14 after it may have been reflected by a blood vessel wall 11. This mechanism may create a less blood recirculation in a reverse blood lines configuration.

Also, comparing FIG. 1 and FIG. 5, those skilled in the art will recognize that extending a distance between a first distal tip opening 14 of a first distal tip segment 12 and a side opening 17 of a second distal tip segment 13, to be more than 30 mm, this configuration may minimize a blood recirculation in a reverse blood lines configuration as well as in a forward blood lines configuration.

The invention claimed is:

1. A hemodialysis curved split-tip catheter comprising:
an elongated body portion having a longitudinal axis, a proximal end and a distal end;
the distal end comprising a first distal tip segment having a first lumen, a tip, and a first distal tip opening;
a second distal tip segment having a second lumen, a sealed portion having a contact point for engaging a blood vessel wall and a side opening, wherein the side hole of the second distal tip segment is located on a wall of the second lumen that faces the first distal tip segment;
the first distal tip segment having an angle with respect to a first axis extended from a dividing point longitudinally parallel to a blood vessel's centerline axis;
the second distal tip segment having a different angle with respect to the first axis to make the hemodialysis curved split-tip catheter in a non-centric configuration inside the blood vessel;
the first distal tip segment having a longer length with respect to the second distal tip segment;
the sealed portion of the second distal tip segment starts from the side opening till a tip of the second distal tip segment; and
wherein the hemodialysis curved split-tip catheter is configured to minimize fibrin sheath formation around the first distal opening and side opening.

2. The hemodialysis curved split-tip catheter of claim 1 wherein in a reverse blood lines configuration, the hemodialysis curved split-tip catheter is configured to have a blood outlet at the side opening of the second distal tip segment having an angle with respect to the blood vessel's centerline axis.

3. The hemodialysis curved split-tip catheter of claim 2 wherein in a reverse blood lines configuration, the hemodialysis curved split-tip catheter is configured to minimize blood recirculation by having a blood outlet at the side opening of the second distal tip segment such that blood is reflected away from a blood inlet at the first distal tip opening of the first distal tip segment.

4. The hemodialysis curved split-tip catheter of claim 1 wherein a lateral length from the dividing point to the side hole of the second distal tip segment is about 30% to about 50% of a lateral length of the second distal tip segment from the dividing point to the tip of the sealed portion.

5. The hemodialysis curved split-tip catheter of claim 1 wherein the angle of the second distal tip segment is larger than the angle of the first distal tip segment.

6. The hemodialysis curved split-tip catheter of claim 1 wherein the first distal tip segment and the second distal tip segment are configured to have a contact point with a blood vessel wall.

\* \* \* \* \*